United States Patent [19]

Litchfield et al.

[11] 4,048,299

[45] Sept. 13, 1977

[54] ANTICARIES CONFECTIONARIES AND ORAL HEALTH PRODUCTS

[75] Inventors: John H. Litchfield, Worthington; Victor G. Vely, Columbus, both of Ohio

[73] Assignee: William Wrigley, Jr. Co., Chicago, Ill.

[21] Appl. No.: 35,246

[22] Filed: May 6, 1970

Related U.S. Application Data

[63] Continuation-in-part of Ser. No. 855,763, Sept. 5, 1969, Pat. No. 3,679,792, Ser. No. 855,764, Sept. 5, 1969, Pat. No. 3,629,395, Ser. No. 855,770, Sept. 5, 1969, Pat. No. 3,749,766, and Ser. No. 858,996, Sept. 18, 1969, Pat. No. 3,651,206, which is a continuation-in-part of Ser. No. 790,314, Jan. 10, 1969, abandoned.

[51] Int. Cl.$^2$ .................... A61K 5/00; A61K 9/68; A61K 7/16
[52] U.S. Cl. ........................ 424/49; 424/48; 424/333; 426/3
[58] Field of Search .................... 424/49–58, 424/333, 48; 426/3

[56] References Cited

U.S. PATENT DOCUMENTS

| | | | |
|---|---|---|---|
| 3,450,812 | 6/1969 | Harris | 424/49 |
| 3,497,590 | 2/1970 | Eigen | 424/55 |

OTHER PUBLICATIONS

Chemical Abstracts, vol. 52, entry 3952f, 1958.
Cutinelli et al., Experientia, June 15, 1967, pp. 437–439.
Egyud, Currents in Modern Biology, published by North-Holland publishing Co., Amsterdam, 1967, vol. 1, pp. 14–20.
Maruzzella et al., Soap, Perfumery & Cosmetics, vol. 34, pp. 743–746, 1961.
Mashimo et al., Sogo Igaku, vol. 10, pp. 805–809, 1953.

*Primary Examiner*—Shep K. Rose
*Attorney, Agent, or Firm*—LeBlanc and Shur

[57] ABSTRACT

Anticaries ingredients for corn and cane sugar containing confectionaries such as syrups, mints, and candies, and for oral health products such as mouthwashes, lozenges, toothpastes and toothpowders are presented. The anticaries ingredients include aliphatic mono and dialdehydes having from 2 to 6 carbon atoms, aliphatic monoaldehydes having from 6 to 12 carbon atoms, and polyaldehydes such as dialdehyde starch and dialdehyde galactomannan gum. These ingredients in concentrations of about 5 percent by weight or less have been found to effectively inhibit the growth and acid production of oral microorganisms and thereby reduce the incidence of dental caries.

16 Claims, No Drawings

ANTICARIES CONFECTIONARIES AND ORAL HEALTH PRODUCTS

This application is a continuation-in-part of our co-pending patent applications Ser. Nos. 855,763; 855,764; and 855,770, filed Sept. 5, 1969, and our co-pending patent application Ser. No. 858,996, filed Sept. 18, 1969, a continuation-in-part of patent application Ser. No. 790,314, filed Jan. 10, 1969, now abandoned. Said prior applications are now, respectively, U.S. Pat. Nos. 3,679,792; 3,629,395; 3,749,766; and 3,651,206.

This invention relates to the prevention of dental caries by incorporating small amounts of anticaries agents in confectionaries, such as syrups, candy, and mints, and oral health problems, such as mouthwash, lozenges, toothpaste, and toothpowder. The anticaries agents of this invention are effective against oral microorganisms and have been found to inhibit the growth and lactic acid production of these microorganisms.

Heretofore, it has been generally known and accepted that the elaboration of acid through the breakdown of readily fermentable carbohydrates by acidogenic oral bacteria is the primary cause of dental caries. The method or mechanism of dental caries is generally characterized by a decalcification of the inorganic portion of the tooth and is accompanied or followed by a disintegration of the organic matrix. If acids are permitted to form on the tooth surface, or once formed if they are not neutralized or otherwise removed, the demineralization of the tooth will proceed.

Dentifrices and similar preparations applied to the tooth surface and gums have been one means customarily employed in the cleaning of teeth. In addition, certain medicated dentifrices having the ability to inhibit tooth decay and control dental caries have been developed and marketed. The inhibiting agents of choice in such medicated dentifrices include fluorides or amides.

Another means for control of dental caries involves the use of sodium fluoride. This component may be added to drinking water or topically applied to tooth surfaces to provide a systemic effect. Sodium fluoride has been accorded some degree of acceptance in this regard. Still another means for control of dental caries involves the use of antibiotics such as penicillin. Antibiotics have produced some desirable results in control of dental caries; but this means is not without certain disadvantages involving sensitization of the patient which thereby limits its value as a means of control of dental caries.

While numerous means have been proposed as potential candidates for inhibiting or neutralizing acid formation in the oral cavity, it appears that the problem of control of dental caries is much more complex. It has definitely been established that application of conventional dentrifice preparations by the consumer once or twice a day is not sufficient to control dental caries. Control of dental caries ideally requires the application of a substance capable of inhibiting acid-producing bacteria in the oral cavity which substance has prolonged effects. Following introduction of the substance into the oral cavity protection must be provided by inhibiting the degradation process during the periods between applications, if not longer. Conventional dentrifices fail to provide such protection, because these dentrifices and their inhibitory additives are soon washed from the oral cavity. Conventional active ingredients are normally in contact with the acid-producing microorganisms an insufficient period of time to achieve prolonged inhibitory effects.

In an effort to provide more effective anticaries treatments it has been discovered that certain aliphatic aldehydes, dialdehydes, polyaldehydes, and certain phosphorous containing compounds exhibit a marked anticaries effect when incorporated in chewing gum. These chewing gum compositions are the subject of our co-pending patent applictions identified as follows: Ser. No. 858,996 filed Sept. 18, 1969, a continuation-in-part of application Ser. No. 790,314 filed Jan. 10, 1969; Ser. No. 855,770, Ser. No. 855,763, and Ser. No. 855,764, all filed Sept. 5, 1969.

The anticaries agents in the chewing gum compositions described in the above patent applications act to inhibit acid forming microorganisms in the mouth during chewing of the gum and for several hours after the gum is discarded. The anticaries chewing gum compositions provide in part a realistic alternative to repeated brushings of the teeth each time food is consumed during the day to neutralize acid on the tooth surface formed by microorganisms normally present in the mouth.

Because the anticaries chewing gum patent applications described above utilize the aldehydes, dialdehydes, and polyaldehydes of this invention as anticaries ingredients in chewing gum the disclosures of the said patent applications are hereby incorporated by reference.

Although a prolonged anticaries effect has been achieved through the use of fluorides as additives in a wide variety of compositions including toothpastes, and drinking water, fluorides primarily act systemically to modify the basic structure of the inorganic portion of the tooth rather than against acid producing mircroorganisms. Because a systemic action is involved the use of fluoride additives in large quantities may have undesirable side effects such as discoloration of the tooth surface. Fluorides therefore are used in dilute concentrations, which although effective to increase resistance to dental caries do not inhibit the cause of dental caries.

The anticaries chewing gum compositions of over above-identified patent applications achieve the desired prolonged anticaries effect without undesirable side effects when used either as a supplement to regular brushing, or as an alternative when brushing is not possible.

However, it has now been discovered, that the aliphatic monoaldehydes, dialdehydes, and polyaldehydes utilized as anticaries ingredients in the chewing gum compositions are capable of broader application, and may successfully be incorporated into a variety of oral health formulations and confectioneries such as sugar syrups, candies, mints, and lozenges. These vehicles introduce effective amounts of the anticaries agents into the mouth, and do not require the mastication associated with chewing gum. When the anticaries agent is released from the vehicle it comes into contact with microorganisms normally present in the mouth, inhibiting bacterial growth and lactic acid production which initiates or is associated with dental caries and pyorrhea.

The use, as anticaries agents, of the following monoaldehydes, dialdehydes, and polyaldehydes is contemplated within the scope of this invention: glyoxal, pyruvaldehyde, glycolaldehyde, d,1-glyceraldehyde, hydroxypropionaldehyde, glutaraldehyde, succinic dialdehyde, 2,4-hexadienal, mesoxalic dialdehyde, 2- hydroxyadipaldehyde, n-hexaldehyde, 2-hexene-1-al, n-heptaldehyde, octanaldehyde, nonanaldehyde, citral, decanaldehyde, undecylic aldehyde, undecylenic aldehyde, dodecyl (lauric) aldehyde, methylnonylacetaldehyde, dialdehyde starch and dialdehyde galactomannan gum.

The preferred anticaries agents specifically utilized in the compositions of this invention are water soluble, low molecular weight, aliphatic mono and dialdehydes such as pyruvaldehyde, glycolaldehyde, d,1-glyceraldehyde, glutaraldehyde and αhydroxypropionaldehyde, higher aliphatic aldehydes such as oil soluble, monoaldehydes having from 8 to 12 carbon atoms, citral of natural origin, polyaldehydes such as dialdehyde starch and dialdehyde galactomannan gum, and mixtures thereof.

Accordingly, it is an object of this invention to provide anticaries ingredients for compositions intended to be ingested, masticated, dissolved, or otherwise taken into the oral cavity whereby the anticaries ingredient comes into contact with microorganisms normally present in the mouth.

It is another object to provide aldehyde compounds adapted to be utilized as ingredients in a wide variety of compositions normally introduced into the mouth which aldehydes upon contact with lactic acid producing microorganisms act to inhibit the growth and acid production of these microorganisms.

It is still another object to provide oral health products such as mouthwash, toothpaste, toothpowder, lozenges, and confectioneries containing significant amounts of cane or corn sugar which contain an anticaries agent effective against oral microorganisms which are associated with dental caries.

It is still another object to provide an anticaries agent comprising one or more low molecular weight mono or dialdehyde, monoaldehydes having from 8 to 12 carbon atoms and polyaldehydes adapted to be blended, dissolved, or otherwise incorporated as in emulsion or a cationic, water-soluble ingredient in oral health products and confectioneries of all types to inhibit the growth of acid production of oral microorganisms.

It is yet another object to provide confectioneries and other foods with anticaries activity by introducing one or more aldehydes in quantities of up to five percent by weight into dextrose or sucrose syrups or solids normally employed in the formulation of confectioneries such as thin mints, hard candy, taffy, and wafers formed by compression, hot-melt, or molding.

These and other objects will become readily apparent with reference to the following discussion.

In accordance with the above objects, it has been discovered that aldehydes of the class described exhibit excellent inhibition of lactic acid formation and growth of oral streptococci and bacilli. As a result of extensive tests, studies and experimentation, both in vitro and in vivo of these compounds in the vehicles above described, it has been observed that they exhibit excellent inhibition of lactic acid formation and growth of oral microorganisms of the genera, Lactobacillus and Streptococcus and related microorganisms found in the oral cavity. Additionally, it has been observed that these compounds are readily incorporated into the vehicles of this invention and are released therefrom upon entry into the oral cavity in quantities sufficient to provide the level of activity desired for control of dental caries.

The anticaries ingredients of this invention are well known aldehydes, and with the exception of pyruvaldehyde, available in forms of a purity applicable to incorporation in foods. Pyruvaldehyde is obtained as an aqueous distillate or as an aqueous phase from a condensed azeotrope. It is nearly colorless, contains approximately 20 to 60 percent substantially pure pyruvaldehyde and contains less than 0.04 percent formaldehyde. This process is described in co-pending patent application Ser. No. 714,793 filed Mar. 21, 1968, now U.S. Pat. No. 3,607,943 and assigned to the assignee of this invention. Further purification may provide a formaldehyde content of less than 0.02 percent by weight as outlined in co-pending patent application Ser. No. 714,807 filed Mar. 21, 1968 now U.S. Pat. No. 3,657,074 and also assigned to the assignee of this invention.

Tables I, II and III following summarize in vivo evaluations of representative aldehydes. Standard laboratory techniques were used to complie the data presented. In each case the aldehyde was incorporated into each specimen's food in a one percent, by weight, quantity, over a period of several weeks. In all cases, caries reduction was noted. As tabulated in Tables I, II and III, each of the aldehydes tested exhibited significant reduction in both the incidence of dental caries and the extent of dental caries in laboratory animals.

The aldehydes tested in vivo were pyruvaldehyde, d,1-glyceraldehyde, crystalline dimer, glycolaldehyde, octanaldehyde, nonanaldehyde, decanaldehyde, undecylenic aldehyde, and lauric aldehyde. The polyaldehydes tested were dialdehyde starch, dialdehyde starch 50 percent oxidized, dialdehyde starch 90 percent oxidized, and dialdehyde galactomannan gum.

Two types of in vitro evaluations of the anticaries agents of this invention were conducted. Tables IV - XII summarize anticaries activity in the form of acid production inhibition and growth inhibition of the anticaries agents of this invention employed against *Streptococcus* or *Lactobacillus* organisms, or against mixed oral organisms from human subjects. The data was compiled through well-known broth tube analysis techniques.

Tables IV - VII summarize the acid production inhibition against specific strains and against mixed oral organisms of varying concentrations of pyruvaldehyde, d,1-glyceraldehyde, glycolaldehyde, and mixtures thereof. Table VIII summarizes the anticaries activity of glycolaldehyde dimer, pyruvaldehyde, propionaldehyde, α-hydroxypropionaldehyde, β-hydroxypropionaldehyde, and d,1-glyceraldehyde.

Tables IX - XI summarize the anticaries activity of aliphatic $C_6$ - $C_{12}$ monoaldehydes. Tables IX and X illustrate the activity against specific strains of oral microorganisms while Table IX illustrates the activity of 2,4-hexadienal against mixed oral microorganisms. Table XII summarizes the activity of di and poly aldehydes against specific strains of *Lactobacillus* and *Streptococcus* acid-producing microorganisms.

Other in vitro evaluations utilized a broth tube analysis of representative anticaries aldehydes incorporated in the vehicles of this invention against cultures of acid producing microorganisms normally present in the mouth. Tables XIII - XIX summarize the results thereof. Standard laboratory procedures were utilized throughout to evaluate the acid production inhibition and growth inhibition over the incubation time of up to 24 hours.

TABLE I.

SUMMARY OF IN VIVO EVALUATIONS OF PYRUVALDEHYDE, GLYCERALDEHDYE AND GLYCOLALDEHYDE BY STANDARD METHODS OF EVALUATION[a]

| Agent | Elapsed Test Days | Number of Animals | Strain and Animal | Caries Score Mean Incidence | Caries Score Mean Extent | Evaluated Caries Reduction[b] | Statistical Evaluation Caries Incidence Reduction | Statistical Evaluation Caries Extent Reduction |
|---|---|---|---|---|---|---|---|---|
| Pyruvaldehyde | 90 | 8 | Osborne-Mendel strain 1, rat | 8.6 | 21.7 | +++ | Significant | Significant |
| Control (RCD diet) | | 7 | " | 23.3 | 64.8 | | | |
| Pyruvaldehyde | 90 | 20 | Osborne-Mendel strain 2, rat | 5.95 | 14.55 | ++ | Significant | Significant |
| Control (L-2000 diet) | | 20 | " | 15.08 | 38.80 | | | |
| Glyceraldehyde | 56 | 8 | Albino, Hamster | 8.0 | 21.8 | +++ | Significant | Significant |
| Control (L-2000 diet) | | 8 | | 27.5 | 80.9 | | | |
| Glyceraldehyde, crystalline dimer | 91 | 8 | Osborne-Mendel strain 2, rat | 15.0 | 29.4 | ++ | Significant | Significant |
| Control (L-2000 diet) | | 8 | | 23.5 | 51.0 | | | |
| Glycolaldehyde | 90 | 20 | Osborne-Mendel strain 1, rat | 5.53 | 13.19 | ++ | Significant | Significant |
| Control (RCD Diet) | | 20 | | 12.85 | 35.45 | | | |
| Glycolaldehyde | 90 | 20 | Osborne-Mendel strain 2, rat | 5.44 | 11.69 | ++ | Significant | Significant |
| Control (L-2000 diet) | | 20 | | 13.94 | 35.38 | | | |

[a]Agents were incorporated in the diet at a 1 percent level.
[b]Symbols designate the following approximate degree of caries reduction: ++ 50 percent, +++ 75 percent.
[c]Evaluated by Student's test at the 95 percent confidence limit.

TABLE II.

SUMMARY OF IN VIVO EVALUATIONS OF ALDEHYDES BY STANDARD METHODS OF EVALUATION[a]

| Agent | Elapsed Test Days | Number of Animals | Strain and Animal | Caries Score Mean Incidence | Caries Score Mean Extent | Evaluated Caries Reduction[b] | Statistical Evaluation[c] Caries Incidence Reduction | Statistical Evaluation[c] Caries Extent Reduction |
|---|---|---|---|---|---|---|---|---|
| Octanaldehyde | 90 | 9 | Osborne-Mendel strain 1, rat | 9.8 | 20.4 | ++ | Significant | Significant |
| Control (RCD diet) | 90 | 7 | " | 19.0 | 49.6 | | | |
| Octanaldehyde | 90 | 10 | Osborne-Mendel strain 2, rat | 2.9 | 4.1 | +++ | Significant | Significant |
| Control (L2000 diet) | 90 | 9 | " | 17.4 | 31.3 | | | |
| Octanaldehyde | 59 | 7 | Albino, Hamster | 18.6 | 53.8 | ++ | Significant | Significant |
| Control (L2000 diet) | 59 | 8 | " | 39.3 | 117.6 | | | |
| Nonanaldehyde | 90 | 7 | Osborne-Mendel strain 1, rat | 5.1 | 10.2 | +++ | Significant | Significant |
| Control (RCD diet) | 90 | 7 | " | 14.1 | 34.3 | | | |
| Decanaldehyde | 90 | 7 | " | 10.4 | 24.1 | ++ | Significant | Significant |
| Control (RCD diet) | 90 | 7 | " | 17.6 | 46.0 | | | |
| Undecylenic aldehyde | 90 | 6 | " | 7.4 | 16.4 | +++ | Significant | Significant |
| Control (RCD diet) | 90 | 5 | " | 22.3 | 54.6 | | | |
| Lauric aldehyde | 90 | 10 | Osborne-Mendel strain 2, rat | 10.0 | 15.6 | ++ | Significant | Significant |
| Control (L2000 diet) | 90 | 9 | " | 17.4 | 31.3 | | | |

[a]Agents were incorporated in the diet at a 1 percent level.
[b]Symbols designate the following approximate degree of caries reduction: ++ 50 percent, +++ 75 percent
[c]Evaluated by Student's test at the 95 percent confidence limit.

TABLE III.

SUMMARY OF IN VIVO EVALUATION OF DIALDEHYDE STARCHES AND POLYSACCHARIDE GUM DETERMINED BY STANDARD METHODS OF EVALUATION[a]

| Agent | Elapsed Test Days | Number of Animals on Test | Strain and Animal | Caries Score Mean Incidence | Caries Score Mean Extent | Evaluated Caries Reduction[b] |
|---|---|---|---|---|---|---|
| Dasol A (water-soluble dialdehyde starch) | 56 | 8 | Syrian hamster | 2.0 | 6.0 | + |
| Controls (fortified L-2000 diet) | 56 | 8 | Syrian hamster | 5.8 | 18.0 | — |
| Dialdehyde starch 50% oxidized | 91 | 10 | Osborne-Mendel strain 1 rat | 14.8 | 38.0 | + |
| Controls (fortified RCD diet) | 91 | 10 | Osborne-Mendel strain 1 rat | 17.8 | 45.8 | — |
| Dialdehyde starch 50% oxidized | 89 | 9 | Osborne-Mendel strain 2 rat | 5.9 | 12.7 | ++ |
| Controls (L-2000 diet) | 89 | 8 | Osborne-Mendel strain 2 rat | 9.5 | 21.5 | — |
| Dialdehyde starch 90% oxidized | 92 | 6 | Osborne-Mendel strain 1 rat | 7.0 | 13.5 | ++ |
| Controls (RCD diet) | 92 | 6 | Osborne-Mendel strain 1 rat | 13.8 | 33.3 | — |
| Dialdehyde galactomannan gum | 90 | 7 | Osborne-Mendel strain 1 rat | 15.7 | 42.9 | + |
| Controls | | | Osborne-Mendel | | | |

TABLE III.-continued
SUMMARY OF IN VIVO EVALUATION OF DIALDEHYDE STARCHES AND POLYSACCHARIDE GUM DETERMINED BY STANDARD METHODS OF EVALUATION[a]

| Agent | Elapsed Test Days | Number of Animals on Test | Strain and Animal | Caries Score Mean Incidence | Mean Extent | Evaluated Caries Reduction[b] |
|---|---|---|---|---|---|---|
| (RCD diet) Dialdehyde galactomannan gum | 90 | 7 | strain 1 rat | 23.3 | 64.8 | — |
|  | 90 | 8 | Osborne-Mendel strain 2 rat | 3.4 | 5.0 | + |
| Controls (L-2000 diet) | 90 | 8 | Osborne-Mendel strain 2 rat | 6.3 | 10.6 | — |

[a]Dialdehyde starches and polysaccharide gum were incorporated in the diet at a 1% level.
[b]Symbols designate the following approximate degrees of reduction: + 25%, ++ 50%.

TABLE IV.
INHIBITORY EFFECTS OF ALDEHYDE COMBINATIONS ON ACID PRODUCTION BY SPECIFIC ORAL MICROORGANISMS(a)

| Concentration, percent | | Organism | Acid Production Inhibition, percent |
|---|---|---|---|
| Pyruvaldehyde d, | 1-Glyceraldehyde | | |
| — | 0.01 | Streptococcus sp. FA-1 | 4 |
| — | 0.015 | " | 10 |
| — | 0.02 | " | 21 |
| 0.001 | — | " | 10 |
| 0.001 | 0.01 | " | 16 |
| 0.001 | 0.015 | " | 44 |
| 0.001 | 0.02 | " | 60 |
| 0.002 | — | " | 35 |
| 0.002 | 0.01 | " | 70 |
| 0.002 | 0.015 | " | 89 |
| 0.002 | 0.02 | " | 91 |
| — | 0.02 | Lactobacillus casei | 11 |
| — | 0.03 | " | 17 |
| — | 0.04 | " | 22 |
| 0.005 | — | " | 24 |
| 0.005 | 0.02 | " | 43 |
| 0.005 | 0.03 | " | 58 |
| 0.005 | 0.04 | " | 72 |
| 0.0075 | — | " | 57 |
| 0.0075 | 0.02 | " | 83 |
| 0.0075 | 0.03 | " | 89 |
| 0.0075 | 0.04 | " | 93 |

(a)Measured by broth-tube technique.

TABLE V.
INHIBITORY EFFECTS OF ALDEHYDE COMBINATIONS ON ACID PRODUCTION BY MIXED ORAL MICROORGANISMS(a)

| Concentration, percent | | Organism | Acid Production Inhibition, percent |
|---|---|---|---|
| Pyruvaldehyde d, | 1-Glyceraldehyde | | |
| — | 0.03 | Mixed Oral Microorganisms | 7 |
| — | 0.04 | " | 12 |
| — | 0.05 | " | 19 |
| — | 0.06 | " | 30 |
| — | 0.07 | " | 40 |
| 0.005 | — | " | 5 |
| 0.005 | 0.03 | " | 18 |
| 0.005 | 0.04 | " | 22 |
| 0.005 | 0.05 | " | 36 |
| 0.005 | 0.06 | " | 49 |
| 0.005 | 0.07 | " | 56 |
| 0.007 | — | " | 5 |
| 0.007 | 0.03 | " | 26 |
| 0.007 | 0.04 | " | 30 |
| 0.007 | 0.05 | " | 44 |
| 0.007 | 0.06 | " | 60 |
| 0.007 | 0.07 | " | 65 |
| 0.009 | — | " | 7 |
| 0.009 | 0.03 | " | 27 |
| 0.009 | 0.04 | " | 28 |
| 0.009 | 0.05 | " | 49 |
| 0.009 | 0.06 | " | 62 |
| 0.009 | 0.07 | " | 68 |
| 0.011 | — | " | 7 |
| 0.011 | 0.03 | " | 37 |
| 0.011 | 0.04 | " | 53 |
| 0.011 | 0.05 | " | 63 |
| 0.011 | 0.06 | " | 66 |

(a)Measured by broth-tube technique.

TABLE VI.

INHIBITORY EFFECTS OF ALDEHYDE COMBINATIONS ON ACID PRODUCTION BY SPECIFIC ORAL MICROORGANISMS(a)

| Concentration, percent | | Organism | Acid Production |
|---|---|---|---|
| Pyruvaldehyde | Glycolaldehyde | | Inhibition, percent |
| — | 0.02 | Streptococcus sp. FA-1 | 19 |
| — | 0.03 | " | 39 |
| — | 0.04 | " | 72 |
| 0.001 | — | " | 10 |
| 0.001 | 0.02 | " | 38 |
| 0.001 | 0.03 | " | 79 |
| 0.001 | 0.04 | " | 96 |
| 0.002 | — | " | 35 |
| 0.002 | 0.02 | " | 90 |
| 0.002 | 0.03 | " | 96 |
| 0.002 | 0.04 | " | 98 |
| — | 0.02 | Lactobacillus casei | 18 |
| — | 0.025 | " | 23 |
| — | 0.03 | " | 27 |
| 0.005 | — | " | 24 |
| 0.005 | 0.02 | " | 44 |
| 0.005 | 0.03 | " | 56 |
| 0.0075 | — | " | 57 |
| 0.0075 | 0.02 | " | 67 |
| 0.0075 | 0.025 | " | 71 |
| 0.0075 | 0.03 | " | 77 |

(a)Measured by broth-tube technique.

TABLE VII.

INHIBITORY EFFECTS OF ALDEHYDE COMBINATIONS ON ACID PRODUCTION BY SPECIFIC ORAL MICROORGANISMS(a)

| Concentration, percent | | Organism | Acid Production |
|---|---|---|---|
| d, 1-Glyceraldehyde | Glycolaldehyde | | Inhibition, percent |
| — | 0.02 | Streptococcus sp. FA-1 | 19 |
| — | 0.03 | " | 39 |
| — | 0.04 | " | 72 |
| 0.01 | — | " | 4 |
| 0.01 | 0.02 | " | 13 |
| 0.01 | 0.03 | " | 32 |
| 0.01 | 0.04 | " | 71 |
| 0.015 | — | " | 10 |
| 0.015 | 0.02 | " | 14 |
| 0.015 | 0.03 | " | 37 |
| 0.015 | 0.04 | " | 89 |
| 0.02 | — | " | 21 |
| 0.02 | 0.02 | " | 24 |
| 0.02 | 0.03 | " | 47 |
| 0.02 | 0.04 | " | 85 |
| — | 0.02 | Lactobacillus casei | 18 |
| — | 0.025 | " | 23 |
| — | 0.03 | " | 27 |
| 0.02 | — | " | 11 |
| 0.02 | 0.02 | " | 22 |
| 0.02 | 0.025 | " | 23 |
| 0.02 | 0.03 | " | 32 |
| 0.03 | — | " | 17 |
| 0.03 | 0.02 | " | 25 |
| 0.03 | 0.025 | " | 29 |
| 0.03 | 0.03 | " | 35 |
| 0.04 | — | " | 22 |
| 0.04 | 0.02 | " | 33 |
| 0.04 | 0.025 | " | 37 |
| 0.04 | 0.03 | " | 44 |

(a)Measured by broth-tube technique.

TABLE VIII.

CARIOSTATIC COMPOUNDS AND RELATED STRUCTURES; COMPARISON OF ACTIVITY AGAINST ORAL MICROORGANISMS IN VITRO

| Compound | | | |
|---|---|---|---|
| Formula | | | |
| Empirical | Structural | Name | Activity(a) |
| $(C_2H_4O_2)_2$ | $(HOCH_2CHO)_2$ | Glycolaldehyde, dimer | ++++ |
| $C_3H_4O_2$ | $CH_3COCHO$ | Pyruvaldehyde | +++ |
| $C_3H_6O$ | $CH_3CH_2CHO$ | Propionaldehyde | + |
| $C_3H_6O_2$ | $CH_3CHOCHO$ | α-Hydroxypropionaldehyde | +++ |
| $C_3H_6O_2$ | $HOCH_2CH_2CHO$ | β-Hydroxypropionaldehyde | +− |
| $C_3H_6O_3$ | $HOCH_2CHOHCHO$ | Glyceraldehyde | ++++ |

(a)Symbols designate the following degree of inhibition:

| | For Acid-Production Inhibition, percent | | For Growth Inhibition, percent |
|---|---|---|---|
| − | 0 to 9 | − | 0 to 75 |

TABLE VIII.-continued
CARIOSTATIC COMPOUNDS AND RELATED STRUCTURES; COMPARISON OF ACTIVITY AGAINST ORAL MICROORGANISMS IN VITRO

| | | | |
|---|---|---|---|
| +− | 10 to 24 | +− | 75 to 89 |
| + | 25 to 74 | + | 90 to 98 |
| ++ | 75 to 89 | ++ | 99 to 99.89 |
| +++ | 90 to 98 | +++ | 99.9 to 99.989 |
| ++++ | 99 to 100 | ++++ | >99.99 |

TABLE IX.
POTENTIAL CARIOSTATIC ACTIVITY OF ALDEHYDES AS DEMONSTRATED BY GROWTH INHIBITION OF ORAL MICROORGANISMS IN VITRO(a)

| Number | Compound | Oral Microorganism | Control | Experimental | Inhibition percent |
|---|---|---|---|---|---|
| 1 | n-Hexaldehyde | Streptococcus spp. FA-1 | $5 \times 10^8$ | $4 \times 10^8$ | Insignificant |
| | | L. casei | $1 \times 10^9$ | $1 \times 10^9$ | None |
| 2 | 2-Hexene-1-al | Streptococcus spp. FA-1 | $4 \times 10^8$ | $9 \times 10^7$ | Insignificant |
| | | L. casei | $9 \times 10^8$ | $8 \times 10^8$ | Insignificant |
| 3 | n-Heptaldehyde | Streptococcus spp. FA-1 | $4 \times 10^8$ | $3 \times 10^8$ | Insignificant |
| | | L. casei | $1 \times 10^9$ | $1 \times 10^9$ | None |
| 4 | Octanaldehyde | Streptococcus spp. FA-1 | $2 \times 10^8$ | $9 \times 10^3$ | >99.99 |
| | | L. casei | $8 \times 10^8$ | $2 \times 10^7$ | 97 |
| 5 | Nonanaldehyde | Streptococcus spp. FA-1 | $2 \times 10^8$ | 0 | 100 |
| | | L. casei | $8 \times 10^8$ | $4 \times 10^4$ | >99.99 |
| 6 | Decanaldehyde | Streptococcus spp. FA-1 | $2 \times 10^8$ | 0 | 100 |
| | | L. casei | $8 \times 10^8$ | $4 \times 10^2$ | >99.99 |
| 7 | Undecylic aldehyde | Streptococcus spp. FA-1 | $5 \times 10^8$ | $2 \times 10^3$ | >99.99 |
| | | L. casei | $9 \times 10^8$ | $5 \times 10^4$ | >99.99 |
| 8 | Undecylenic aldehyde | Streptococcus spp. FA-1 | $2 \times 10^8$ | 0 | 100 |
| | | L. casei | $8 \times 10^8$ | $1 \times 10^2$ | >99.99 |
| 9 | Lauric aldehyde | Streptococcus spp. FA-1 | $2 \times 10^8$ | 0 | 100 |
| | | L. casei | $8 \times 10^8$ | $<1 \times 10^2$ | >99.99 |
| 10 | Methylnonylacetaldehyde | Streptococcus spp. FA-1 | $2 \times 10^8$ | 0 | 100 |
| | | L. casei | $8 \times 10^8$ | $<1 \times 10^3$ | >99.99 |

(a)Determined on freshly grown pure cultures. Pour plates were incubated 48 - 72 hours.

TABLE X.
CARIOSTATIC ACTIVITY OF ALDEHYDES AS DEMONSTRATED BY INHIBITION OF ACID PRODUCTION BY ORAL MICROORGANISMS IN VITRO

| Compound FORMULA | | | Activity(a), Acid- |
|---|---|---|---|
| Empirical | Structural | Name | Production Inhibition% |
| $C_6H_{12}O$ | $CH_3(CH_2)_4CHO$ | n-Hexaldehyde | + |
| $C_6H_{10}O$ | $CH_3(CH_2)_2CH:CHCHO$ | 2-Hexene-1-al | +++ |
| $C_7H_{14}O$ | $CH_3(CH_2)_5CHO$ | n-Heptaldehyde | ++ |
| $C_8H_{16}O$ | $CH_3(CH_2)_6CHO$ | Octanaldehyde | ++++ |
| $C_9H_{18}O$ | $CH_3(CH_2)_7CHO$ | Nonanaldehyde | ++++ |
| $C_{10}H_{16}O$ | $CH_3CCH_3:CH(CH_2)_2C:CHCHO$ | Citral | ++++ |
| $C_{10}H_{20}O$ | $CH_3(CH_2)_8CHO$ | Decanaldehyde | ++++ |
| $C_{11}H_{22}O$ | $CH_3(CH_2)_9CHO$ | Undecylic aldehyde | ++++ |
| $C_{11}H_{20}O$ | $CH_3CH:CH(CH_2)_7CHO$ | Undecylenic aldehyde | ++++ |
| $C_{12}H_{24}O$ | $CH_3(CH_2)_{10}CHO$ | Lauric aldehyde | ++++ |
| $C_{12}H_{24}O$ | $CH_3(CH_2)_8CHCH_3CHO$ | Methylnonylacetaldehyde | +++ |

(a)Activity was measured by broth-tube assay to determine percent of acid-production inhibition obtained by Lactobacillus casei and Streptococcus sp. FA-1 in the presence of 0.1 percent of compound. Symbols designate the following degree of inhibition percent:

| | | | |
|---|---|---|---|
| − | 0 to 9 | ++ | 75 to 89 |
| +− | 10 to 24 | +++ | 90 to 98 |
| + | 25 to 74 | ++++ | 99 to 100 |

TABLE XI.
EFFECTIVENESS OF 2,4-HEXADIENAL AGAINST ORAL MICROORGANISMS IN VITRO(a)

| Tube | Compound Concentration, percent | Inhibition of Acid Production, percent | | |
|---|---|---|---|---|
| | | Streptococcus sp. FA-1 | Streptococcus sp. GS-5 | Lactobacillus casei |
| 1 | 0.01 | 31 | 8 | 27 |
| 2 | 0.025 | 92 | 35 | 43 |
| 3 | 0.05 | 99 | 97 | 88 |
| 4 | 0.075 | 99 | 99 | 94 |
| 5 | 0.10 | 100 | 100 | 98 |

(a)2,4-Hexadienal was prepared as an emulsion with 4 parts of Tween 20.

TABLE XII.

CARIOSTATIC ACTIVITY OF DIALDEHYDES AGAINST ORAL MICROORGANISMS IN VITRO

| Number | Compound Formula Empirical | Structural | Name | Activity[a] Acid-Production Inhibition, % |
|---|---|---|---|---|
| 1 | $C_2H_2O_2$ | OHCCHO | Glyoxal | +++ |
| 2 | $C_3H_2O_3$ | OHCCOCHO | Mesoxalic dialdehyde | +[b] |
| 3 | $C_3H_4O_3$ | OHCCHOHCHO | Tartronic dialdehyde | +[c] |
| 4 | $C_4H_4O_2$ | OHCCH:CHCHO | Fumaricaldehyde | +[c] |
| 5 | $C_4H_6O_2$ | $OHCCH_2CH_2CHO$ | Succinic dialdehyde | ++++ |
| 6 | $C_4H_6O_3$ | $OHCCHOHCH_2CHO$ | α-Hydroxysuccindialdehyde | +[c] |
| 7 | $C_5H_8O_2$ | $OHC(CH_2)_3CHO$ | Glutaraldehyde | ++++ |
| 8 | $C_6H_6O_2$ | OHCCH:CHCH:CHCHO | 2,4-Hexadienal | ++++ |
| 9 | $C_6H_{10}O_2$ | $OHC(CH_2)_4CHO$ | Adipaldehyde (hexanedial) | +[c] |
| 10 | $C_6H_{10}O_3$ | $OHC(CH_2)_3CHOHCHO$ | 2-Hydroxyadipaldehyde | + |
| 11 | $[C_6H_8O_5]_n$ | $\begin{bmatrix} C\ H & C\ H & O & C\ H\ O \\ \|\quad & \|\quad & & \|\quad \\ CHO & CH_2OH & & CHO \end{bmatrix}_n$ | Dialdehyde starch (water soluble cationic) | + |
| 12 | | | Dialdehyde galactomannan gum (an oxidized polysaccharide) | + |

[a] Activity was measured by broth-tube assay to determine percent of acid-production inhibition obtained by *Lactobacillus casei* and *Streptococcus* sp. FA-1 in the presence of 0.1% of compound. Symbols designate the following degree of inhibition, percent:
 − 0 to 9    ++ 75 to 89
 +− 10 to 24   +++ 90 to 98
 + 25 to 74   ++++ 99 to 100

[b] Confirmation of purity and structure was lacking for this compound. Actual activity could be much higher.
[c] These compounds are not available commercially and therefore were not tested in vitro. However, the compounds noted should exhibit the activity shown, and if synthesized, they would be expected to exhibit good anti-caries qualities.

TABLE XIII.

EFFECT OF ALDEHYDES IN SUCROSE SYRUP ON ORAL MICROOGRAMISMS

| Aldehyde | Microorganism | Incubation Time, Hours | Inhibition, Per cent Acid Production(a) | Growth(b) |
|---|---|---|---|---|
| Glycolaldehyde | Lactobacillus casei ATCC 4646 | 2 | 0 | N.S.(c) |
| | | 5 | 0 | 93 |
| | | 24 | 86 | >99.99 |
| | Streptococcus spp. KI-R | 2 | 19 | 80 |
| | | 5 | 85 | >99.9 |
| | | 24 | 84 | >99.99 |
| | Mixed human oral microorganisms | 2 | 44 | 98 |
| | | 5 | 90 | >99.99 |
| | | 24 | 85 | >99 |
| Pyruvaldehyde | Lactobacillus casei ATCC 4646 | 2 | 0 | 97.5 |
| | | 5 | 20.0 | >99.99 |
| | | 24 | 89.6 | >99.99 |
| | Streptococcus spp. KI-R | 2 | 37.5 | >99.9 |
| | | 5 | 82.3 | >99.99 |
| | | 24 | 86.4 | 100 |
| | Mixed human oral microorganisms | 2 | 77.8 | >99.9 |
| | | 5 | 92.1 | >99.99 |
| | | 24 | 91.8 | N.S. |
| d,1-Glyceraldehyde | Lactobacillus casei ATCC 4646 | 2 | 0 | 0 |
| | | 5 | 30 | N.S. |
| | | 24 | 79 | 99 |
| | Streptococcus spp. KI-R | 2 | 69 | 90 |
| | | 5 | 88 | 90 |
| | | 24 | 86 | 99 |
| | Mixed human oral microorganisms | 2 | 72 | 96 |
| | | 5 | 93 | 99.6 |
| | | 24 | 16 | 0 |
| Glutaraldehyde | Lactobacillus casei ATCC 4646 | 2 | 100 | N.S. |
| | | 5 | 75 | >N.S. |
| | | 24 | 50 | N.S. |
| | Streptococcus spp. KI-R | 2 | 100 | N.S. |
| | | 5 | 83 | >99 |
| | | 24 | 0 | 90 |
| | Mixed human oral microorganisms | 2 | 100 | 90 |
| | | 5 | 59 | 93 |
| | | 24 | 0 | N.S. |
| Decylaldehyde | Lactobacillus casei ATCC 4646 | 2 | 0 | 99.5 |
| | | 5 | 95 | >99.9 |
| | | 24 | 99 | >99.99 |
| | Streptococcus spp. KI-R | 2 | 75 | >99.99 |
| | | 5 | 98 | >99.99 |
| | | 24 | 100 | N.S. |
| | Mixed human oral microorganisms | 2 | 78 | >99.99 |
| | | 5 | 94 | >99.99 |

TABLE XIII.-continued
EFFECT OF ALDEHYDES IN SUCROSE SYRUP ON ORAL MICROOGRAMISMS

| Aldehyde | Microorganism | Incubation Time, Hours | Inhibition, Per cent Acid Production(a) | Growth(b) |
|---|---|---|---|---|
| | | 24 | 95 | N.S. |

(a)Measured by broth-tube technique.
(b)Measured by pour-plate technique.
(c)N.S. designates not significant.

TABLE XIV.
EFFECT OF ALDEHYDES IN DEXTROSE SYRUP ON ORAL MICROORGANISMS

| Aldehyde | Microorganism | Incubation Time, Hours | Inhibition, Per Cent Acid Production(a) | Growth(b) |
|---|---|---|---|---|
| Glycolaldehyde | Lactobacillus casei ATCC 4646 | 2 | 33 | N.S.(c) |
| | | 5 | 3 | 98 |
| | | 24 | 85 | 100 |
| | Streptococcus spp. KI-R | 2 | 57 | 99.1 |
| | | 5 | 81 | 100 |
| | | 24 | 77 | 100 |
| | Mixed human oral microorganisms | 2 | 15 | 99 |
| | | 5 | 87 | 100 |
| | | 24 | 87 | 91.4 |
| Pyruvaldehyde | Lactobacillus casei ATCC 4646 | 2 | 52 | 99.4 |
| | | 5 | 33 | 99.99 |
| | | 24 | 88 | 100 |
| | Streptococcus spp. KI-R | 2 | 57 | 100 |
| | | 5 | 86 | 100 |
| | | 24 | 82 | 100 |
| | Mixed human oral microorganisms | 2 | 15 | 99.8 |
| | | 5 | 89 | 100 |
| | | 24 | 83 | 99.99 |
| d,1-Glyceraldehyde | Lactobacillus casei ATCC 4646 | 2 | 57 | N.S. |
| | | 5 | 33 | N.S. |
| | | 24 | 89 | >99.99 |
| | Streptococcus Spp. KI-R | 2 | 48 | 98 |
| | | 5 | 86 | >99.99 |
| | | 24 | 82 | >100 |
| | Mixed human oral microorganisms | 2 | 8 | 97.5 |
| | | 5 | 90 | >99.99 |
| | | 24 | 77 | 0 |
| Glutaraldehyde | Lactobacillus casei ATCC 4646 | 2 | 76 | N.S. |
| | | 5 | 70 | N.S. |
| | | 24 | 29 | 90 |
| | Streptococcus spp. KI-R | 2 | 70 | N.S. |
| | | 5 | 93 | 99.96 |
| | | 24 | 0 | 0 |
| | Mixed human oral microorganisms | 2 | 23 | 92.5 |
| | | 5 | 81 | 90 |
| | | 24 | 16 | N.S. |
| Decylaldehyde | Lactobacillus casei ATCC 4646 | 2 | 67 | 99.7 |
| | | 5 | 77 | 100 |
| | | 24 | 96 | 100 |
| | Streptococcus spp. KI-R | 2 | 35 | 100 |
| | | 5 | 91 | 100 |
| | | 24 | 89 | 100 |
| | Mixed human oral microorganisms | 2 | 0 | >99.99 |
| | | 5 | 95 | 100 |
| | | 24 | 91 | 100 |

(a)Same as in Table XIII.
(b)Same as in Table XIII.
(c)Same as in Table XIII.

TABLE XV
EFFECT OF ALDEHYDES IN COMPRESSED CANDY TABLET ON ORAL MICROORGANISMS

| Aldehyde | Microorganisms | Incubation Time, Hours | Inhibition, Per Cent Acid Production(a) | Growth(b) |
|---|---|---|---|---|
| Glycolaldehyde | Lactobacillus casei ATCC 4646 | 2 | 0 | N.S.(c) |
| | | 5 | 0 | 97.3 |
| | | 24 | 64 | 100 |
| | Streptococcus spp. KI-R | 2 | 0 | 99.9 |
| | | 5 | 0 | N.S. |
| | | 24 | 73 | N.S. |
| | Mixed human oral Microorganisms | 2 | 0 | 99.3 |
| | | 5 | 84 | 100 |
| | | 24 | 72 | 100 |
| Pyruvaldehyde | Lactobacillus casei ATCC 4646 | 2 | 0 | 99.5 |
| | | 5 | 0 | 100 |
| | | 24 | 75 | 100 |
| | Streptococcus spp. KI-R | 2 | 0 | N.S. |
| | | 5 | 30 | N.S. |
| | | 24 | 83 | N.S. |
| | Mixed human oral | 2 | 0 | 99.7 |

TABLE XV-continued
EFFECT OF ALDEHYDES IN COMPRESSED CANDY TABLET ON ORAL MICROORGANISMS

| Aldehyde | Microorganisms | Incubation Time, Hours | Inhibition, Per Cent Acid Production(a) | Growth(b) |
|---|---|---|---|---|
| | Microorganisms | 5 | 89 | 99.99 |
| | | 24 | 78 | 99.98 |
| d,1-Glyceraldehyde | Lactobacillus casei ATCC 4646 | 2 | 0 | N.S. |
| | | 5 | 0 | N.S. |
| | | 24 | 73 | 100 |
| | Streptococcus spp. KI-R | 2 | 0 | 0 |
| | | 5 | 25 | N.S. |
| | | 24 | 84 | N.S. |
| | Mixed human oral Microorganisms | 2 | 0 | 99.7 |
| | | 5 | 91 | 99.99 |
| | | 24 | 87 | N.S. |
| Glutaraldehyde | Lactobacillus casei ATCC 4646 | 2 | 0 | N.S. |
| | | 5 | 33 | N.S. |
| | | 24 | 81 | 99.5 |
| | Streptococcus spp. KI-R | 2 | 100 | N.S. |
| | | 5 | 100 | N.S. |
| | | 24 | 100 | N.S. |
| | Mixed human oral Microorganisms | 2 | 100 | 97.3 |
| | | 5 | 100 | 99.8 |
| | | 24 | 0 | N.S. |
| Decylaldehyde | Lactobacillus casei ATCC 4646 | 2 | 0 | 99.98 |
| | | 5 | 67 | 100 |
| | | 24 | 97 | 100 |
| | Streptococcus spp. KI-R | 2 | 50 | N.S. |
| | | 5 | 85 | N.S. |
| | | 24 | 98 | N.S. |
| | Mixed human oral Microoganisms | 2 | 100 | >99.99 |
| | | 5 | 100 | >99.99 |
| | | 24 | 19 | 100 |

(a)Same as in Table XIII.
(b)Same as in Table XIII.
(c)Same as in Table XIII.

TABLE XVI
EFFECT OF PYRUVALDEHYDE IN HARD CANDY ON ORAL MICROORGANISMS

| Microorganism | Incubation Time, Hours | Inhibition, Per Cent Acid Production(a) | Growth(b) |
|---|---|---|---|
| Lactobacillus casei ATCC 4646 | 2 | 0 | 92 |
| | 5 | 22 | 99.85 |
| | 24 | 90 | 100 |
| Streptococcus spp. KI-R | 2 | 40 | >99.99 |
| | 5 | 87 | >99.99 |
| | 24 | 86 | 100 |
| Mixed human oral Microorganisms | 2 | 20 | 99.5 |
| | 5 | 93 | 100 |
| | 24 | 84 | N.S.(c) |

(a)Same as in Table XIII.
(b)Same as in Table XIII.
(c)Same as in Table XIII.

TABLE XVII
EFFECT OF ALDEHYDES IN MOUTHWASH ON ORAL MICROORGANISMS

| Aldehyde | Microorganism | Incubation Time, Hours | Inhibition, Per cent Acid Production(a) | Growth(b) |
|---|---|---|---|---|
| Glycolaldehyde | Streptococcus spp. KI-R | 2 | 0 | 99.98 |
| | | 5 | 0 | 100 |
| | | 24 | 78 | 100 |
| | Mixed human oral Microorganisms | 2 | 0 | 99.7 |
| | | 5 | 87 | 100 |
| | | 24 | 80 | 99.90 |
| Pyruvaldehyde | Streptococcus spp. KI-R | 2 | 0 | >99.99 |
| | | 5 | 0 | >99.99 |
| | | 24 | 86 | 100 |
| | Mixed human oral Microorganisms | 2 | 0 | 99.0 |
| | | 5 | 94 | 100 |
| | | 24 | 87 | 99.7 |
| d,1-Glyceraldehyde | Streptococcus spp. KI-R | 2 | 0 | >99.99 |
| | | 5 | 0 | 99.99 |
| | | 24 | 86 | 100 |
| | Mixed human oral Microorganisms | 2 | 0 | 95.0 |
| | | 5 | 91 | 99.98 |
| | | 24 | 39 | N.S.(c) |
| Glutaraldehyde | Streptococcus spp. KI-R | 2 | 0 | 100 |
| | | 5 | 0 | 99.999 |
| | | 24 | 99 | 100 |
| | Mixed human oral Microorganisms | 2 | 0 | 100 |
| | | 5 | 100 | 100 |
| | | 24 | 91 | 99.9 |

(a)Same as in Table XIII.
(b)Same as in Table XIII.
(c)Same as in Table XIII.

TABLE XVIII

EFFECT OF ALDEHYDES IN TOOTHPASTE ON ORAL MICROORGANISMS

| Aldehydes | Microorganism | Incubation Time, Hours | Inhibition, Per cent Acid Production[a] | Growth[b] |
|---|---|---|---|---|
| Glycolaldehyde | Lactobacillus casei ATCC 4646 | 2 | 0 | 0 |
| | | 5 | 0 | N.S.[c] |
| | | 24 | 0 | 100 |
| | Streptococcus spp. KI-R | 2 | 0 | 0 |
| | | 5 | 0 | N.S. |
| | | 24 | 0 | N.S. |
| | Mixed human oral Microorganisms | 2 | 0 | N.S. |
| | | 5 | 0 | N.S. |
| | | 24 | 0 | 100 |
| Pyruvaldehyde | Lactobacillus casei ATCC 4646 | 2 | 0 | N.S. |
| | | 5 | 0 | N.S. |
| | | 24 | 0 | 100 |
| | Streptococcus spp. KI-R | 2 | 0 | N.S. |
| | | 5 | 0 | N.S. |
| | | 24 | 0 | N.S. |
| | Mixed human oral Microorganisms | 2 | 0 | 100 |
| | | 5 | 0 | N.S. |
| | | 24 | 0 | 100 |
| d,1-Glyceraldehyde Lactobacillus casei | | 2 | 0 | N.S. |
| | ATCC 4646 | 5 | 0 | N.S. |
| | | 24 | 0 | 100 |
| | Streptococcus spp. KI-R | 2 | 0 | N.S. |
| | | 5 | 0 | N.S. |
| | | 24 | 0 | 0 |
| | Mixed human oral Microorganisms | 2 | 0 | 97 |
| | | 5 | 0 | N.S. |
| | | 24 | 0 | 100 |
| Glutaraldehyde | Lactobacillus casei ATCC 4646 | 2 | 80 | N.S. |
| | | 5 | 80 | N.S. |
| | | 24 | 50 | 0 |
| | Streptococcus spp. KI-R | 2 | 100 | N.S. |
| | | 5 | 100 | N.S. |
| | | 24 | 84 | N.S. |
| | Mixed human oral Microorganisms | 2 | 0 | 0 |
| | | 5 | 0 | N.S. |
| | | 24 | 0 | N.S. |
| Decylaldehyde | Lactobacillus casei ATCC 4646 | 2 | 80 | 0 |
| | | 5 | 80 | N.S. |
| | | 24 | 83 | 0 |
| | Streptococcus spp. KI-R | 2 | 40 | 0 |
| | | 5 | 100 | N.S. |
| | | 24 | 67 | N.S. |
| | Mixed human oral Microorganisms | 2 | 0 | N.S. |
| | | 5 | 0 | N.S. |
| | | 24 | 0 | 0 |

[a]Same as in Table XIII.
[b]Same as in Table XIII.
[c]Same as in Table XIII.

TABLE XIX

EFFECT OF ALDEHYDES IN TOOTH POWDER ON ORAL MICROORGANISMS

| Aldehyde | Microorganism | Incubation Time, Hours | Inhibition, Per cent Acid Production[a] | Growth[b] |
|---|---|---|---|---|
| Glycolaldehyde | Lactobacillus casei ATCC 4646 | 2 | 0 | N.S.[c] |
| | | 5 | 0 | N.S. |
| | | 24 | 73 | 99.99 |
| | Streptococcus spp. KI-R | 2 | 0 | N.S. |
| | | 5 | 0 | 93.3 |
| | | 24 | 0 | 100 |
| | Mixed human oral MICROORGANISMS | 2 | 0 | N.S. |
| | | 5 | 82 | 99.97 |
| | | 24 | 77 | 100 |
| Pyruvaldehyde | Lactobacillus casei ATCC 4646 | 2 | 0 | N.S. |
| | | 5 | 98 | 0 |
| | | 24 | 71 | 100 |
| | Streptococcus spp. KI-R | 2 | 0 | 100 |
| | | 5 | 0 | 100 |
| | | 24 | 0 | 100 |
| | Mixed human oral Microorganisms | 2 | 0 | N.S. |
| | | 5 | 86 | 99.99 |
| | | 24 | 80 | 99.94 |
| d,1-Glyceraldehyde | Lactobacillus casei ATCC 4646 | 2 | 0 | N.S. |
| | | 5 | 0 | N.S. |
| | | 24 | 84 | 99.3 |
| | Streptococcus spp. KI-R | 2 | 0 | 99.88 |
| | | 5 | 0 | 99.99 |
| | | 24 | 0 | 100 |
| | Mixed human oral microorganisms | 2 | 0 | N.S. |
| | | 5 | 48 | 99.3 |
| | | 24 | 18 | N.S. |
| Glutaraldehyde | Lactobacillus casei ATCC 4646 | 2 | 0 | N.S. |
| | | 5 | 33 | N.S. |
| | | 24 | 21 | N.S. |
| | Streptococcus spp. | 2 | 0 | N.S. |

TABLE XIX-continued
EFFECT OF ALDEHYDES IN TOOTH POWDER ON ORAL MICROORGANISMS

| Aldehyde | Microorganism | Incubation Time, Hours | Inhibition, Per cent Acid Production[a] | Growth[b] |
|---|---|---|---|---|
| | KI-R | 5 | 0 | N.S. |
| | | 24 | 0 | N.S. |
| | Mixed human oral | 2 | 67 | N.S. |
| | Microorganisms | 5 | 95 | 96.6 |
| | | 24 | 45 | N.S. |
| Dodecylaldehyde | Lactobacillus casei | 2 | 0 | 99.5 |
| | ATCC 4646 | 5 | 0 | >99.99 |
| | | 24 | 93 | 99.99 |
| | Streptococcus spp. | 2 | 0 | 99.2 |
| | KI-R | 5 | 0 | >99.99 |
| | | 24 | 0 | 100 |
| | Mixed human oral | 2 | 33 | 99.8 |
| | Microorganism | 5 | 96 | 99.6 |
| | | 24 | 0 | N.S. |

[a]Same as in Table XIII.
[b]Same as in Table XIII.
[c]Same as in Table XIII.

In formulating Tables XIII – XIX representative aldehydes having anticaries activity were selected from those tested as summarized in Tables I – XII and incorporated in seven representative types of products. The products included dextrose and sucrose syrups, obtained commercially in food grades, and compressed candy, hard candy, mouthwash, toothpaste and toothpowder. The five latter products also employed food grade and reagent grade ingredients. These products were formulated by well-known and representative recipes for each type of product. The products were formed in batches of approximately 1 pound or 1 liter and contained all their normal constitutents. Aliquots of each products were blended with one of each of the representative aldehydes selected except in the case of hard candy.

It should be understood that the use of one or more aldehydes which exist in dimeric or polymerized and hydrated forms are particularly suited to use in hard candy compositions at high temperatures. For example, volatilization and oxidative degradation would be minimized by the chemical structure of glycolaldehyde and pyruvaldehyde. For this reason pyruvaldehyde was used as a representative ingredient in the hard candy tested.

Aliquots of the aldehyde incorporating sugar syrups, confectioneries, and mouthwash formulations were added directly to assay flasks and mixed or dissolved as required. Aqueous extracts of the aldehyde incorporated in toothpaste and toothpowder were prepared and aliquots of the filtrate were added to the assay flasks.

The assay flasks contained the necessary components for a normal growth response from the organisms employed, Lactobacillus casei ATCC 4646, originally a human oral isolate, Streptococcus spp. K1-R, human caries isolate, and a mixed oral microbial population obtained fresh from saliva on the morning prior to the initiation of each assay incubation period. The assay flask medium was dissolved in distilled water in which was added an equal volume of filter sterilized human saliva to yield a 50 percent saliva-medium combination. The medium contained all normal ingredients such as yeast extract, proteose peptone number 3 (a proprietary formula of Difco Laboratories, Detroit, Michigan) monopotassium phosphate, Tween 80 (polyoxyethylene sorbitan monoleate) and water, except a carbon source. This was supplied by the aliquot of the sucrose syrup, dextrose syrup, sucrose in the compressed candy tablet and sucrose in the hard candy product. In addition, an aliquot of sucrose solution concentrate was added to the assay flask as a carbon source for evaluation of mouthwash, toothpaste, and toothpowder vehicles.

Sucrose syrup was prepared from cane sugar and was a 60 percent aqueous solution. The dextrose syrup was a light corn syrup containing about 37 – 38 percent dextrose equivalent.

The following examples list the recipes utilized to formulate vehicles for the anticaries compounds of this invention. The aldehydes of this invention were then incorporated in the vehicles and in vitro anticaries activity was evaluated as summarized in Tables XIII – XIX.

EXAMPLE 1 - COMPRESSED CANDY TABLET

| Ingredients | Parts by Weight |
|---|---|
| Icing sugar, finely sifted | 100 |
| Oil of peppermint | 0.6 |
| Gum arabic, powdered | 1-2 |
| Water | 6 |
| Stearic acid, powdered | 1 |

EXAMPLE 2 - HARD CANDY

| Ingredients | Quantity |
|---|---|
| Sugar, granulated | 0.75 lbs. |
| Corn syrup, light | 4 ozs. |
| Water | 0.33–0.25 cups |

The mixture was cooked to 290° F. and poured into an oiled tray Pyruvaldehyde was added with stirring when the temperature of the batch reached 230° F. and before pouring and solidification of the composition.

EXAMPLE 3 - MOUTHWASH

| Ingredients | Parts by Weight |
|---|---|
| Sodium bicarbonate | 2 |
| Sodium chloride | 0.5 |
| Sucaryl sodium | 0.33 |
| Flavor | 0.8 |
| Ethyl alcohol | 25 |
| Water | 72.12 |

The aldehyde ingredient was added in place of an equivalent amount of water in this and subsequent examples.

EXAMPLE 4 - TOOTHPASTE

| Ingredients | Parts by Weight |
| --- | --- |
| Sodium metaphosphate, insoluble | 26.6 |
| Dicalcium phosphate | 26.6 |
| Gum tragacanth | 1.4 |
| Flavor | 1.6 |
| Sodium lauryl sulphate, food grade | 1.1 |
| Glycerol and water | 42.7 |

The quantity of water in relation to glycerol was found to be critical in the preparation of the toothpaste. Excess water results in a slurry, rather than a paste, with insufficient body.

EXAMPLE 5 - TOOTHPOWDER

| Ingredients | Parts by Weight |
| --- | --- |
| Sodium metaphosphate | 76.8 |
| Tricalcium phosphate | 20 |
| Sodium lauryl sulphate, food grade | 1.0 |
| Flavor | 2.0 |
| Saccharin | 0.2 |

The lower aldehydes such as glycolaldehyde, crystalline dimer; pyruvaldehyde, aqueous syrup; d,1-glyceraldehyde solution and crystalline dimer; and glutaraldehyde, employed as a 50 percent aqueous solution, are water soluble and were employed directly either as powders or aqueous solutions. The $C_8$ to $C_{12}$, longer chain aliphatic aldehydes, of which decyl and dodecyl (lauric) were selected as representative, are oil soluble and are prepared and added to the products as emulsions with four parts of Tween 20, polyoxethylene sorbitan monolaurate. The aldehyde concentrations in the products were randomly chosen between 1 to 5 percent by weight. Limits for the concentrations were selected to coincide with the data presented in Tables I - XII in order to verify that the anticaries activity of the aldehydes in the product vehicles tested was equivalent to the activity previously established for the aldehydes alone.

In summary, Tables I and II above show pyruvaldehyde, d,1-glyceraldehyde, and glycolaldehyde exhibit significant anticaries effects when incorporated in the diet of laboratory animals at a one percent level. Tables IV - VII also show that pyruvaldehyde, d,1-glyceraldehyde, and glycolaldehyde alone or in combination exhibit excellent acid production inhibition in oral microorganisms. Table VIII shows that based on in vitro tests αhydroxypropionaldehyde also exhibits excellent anticaries activity.

Table II shows octanaldehyde, nonanaldehyde, decanaldehyde, undecylenicaldehyde, and lauric aldehyde exhibit significant anticaries activity when incorporated at a one percent level in the diet of laboratory animals. Tables IX - XII verify that the $C_8 - C_{12}$ aliphatic aldehydes exhibit excellent anticaries activity based upon in vitro tests against oral microorganisms. The $C_6$ and $C_7$ aldehydes, n-hexaldehyde, 2-hexene-1-al, 2,4-hexadienal, and n-heptaldehyde exhibited excellent acid production inhibition, but little or no growth inhibition in the oral microorganisms.

Table III shows that on the basis of in vivo testing with laboratory animals polyaldehydes such as dialdehyde starches and polysaccharide gums, specifically Dasol A, dialdehyde starch 50 percent oxidized, dialdehyde starch 90 percent oxidized, and dialdehyde galactamannan gum exhibit significant anticaries reduction when incorporated into the diet of laboratory animals at a one percent level. Table XII verifies the acid production inhibition on the basis of in vitro broth tube assays involving cultures of oral microorganisms.

The effectiveness of the representative aldehydes incorporated in representative product types at concentrations of from 1 to 5 percent is illustrated in Tables XIII - XIX. The tables show that the aldehyde compounds of this invention exhibit a significant degree of growth and acid-production inhibition of oral microorganisms during the 24-hour incubation period.

It should be noted that the data contained in Tables XVII, XVIII, and XIX presented difficulties in that the oral health products utilized as vehicles also contain other materials such as flavor oils and ethyl alcohol which also inhibit acid-production of bacteria. Although the culture strains tested were significantly inhibited by the products tested, the effect attributable to the aldehyde ingredients was not readily isolated. However, on the basis of all tests presented, the aldehydes exhibit a significant and prolonged anticaries activity, such that the results in Tables XVII, XVIII, and XIX merely confirm that this activity is not neutralized and their anticaries activity otherwise dissipated when the aldehydes are incorporated in commercial oral health product formulations.

The invention as presented comprises the use of aliphatic mono and dialdehydes having from two to six carbon atoms, aliphatic monoaldehydes having from six to twelve carbon atoms, polyaldehydes such as dialdehyde starch and dialdehyde galactomannan gum, and mixtures thereof as ingredients in oral health products and confectionery foods to impact a prolonged anticaries activity to these products and foods. The anticaries aldehydes of this invention have been found to significantly inhibit the growth and/or acid-production of oral microorganisms. The use thereof has been found to significantly reduce the incidences and extent of dental caries.

It is contemplated that the aldehydes actually utilized to compile the data in Tables XIII - XIX are representative of the aldehydes tested in Tables I - XII. It is intended that the products tested are illustrative of oral health products and confectionery foods generally. Accordingly, this invention is not intended to be limited to the product formulations utilized or those aldehydes shown to have anticaries activity which were actually incorporated in the illustrative products for testing purposes, but limited only by the following claims.

What is desired to be secured by U.S. Letters Patent is claimed as follows:

1. An oral health composition comprising an effective amount of pyruvaldehyde to inhibit the acid production and growth of oral microorganisms and a dental vehicle.

2. The composition of claim 1 wherein pyruvaldehyde is present in no more than about 5 percent by weight of the total composition.

3. An oral health composition comprising an effective amount of glycoladehyde to inhibit the acid production and growth of oral microorganisms and a dental vehicle.

4. The composition of claim 3 wherein glycoladehyde is present in no more than about 5 percent by weight of the total composition.

5. An oral health composition comprising an effective amount of d,1-glyceraldehyde to inhibit the acid production and growth of oral microorganisms and a dental vehicle.

6. The composition of claim 5 wherein d,l-glyceraldehyde is present in no more than about 5 percent by weight of the total composition.

7. An oral health composition comprising an effective amount of α-hydroxypropionaldehyde to inhibit the acid production and growth of oral microorganisms and a dental vehicle.

8. The composition of claim 7 wherein α-hydroxypropionaldehyde is present in no more than about 5 percent by weight of the total composition.

9. An oral health composition comprising an effective amount of succinic dialdehyde to inhibit the acid production and growth of oral microorganisms and a dental vehicle.

10. The composition of claim 9 wherein succinic dialdehyde is present in no more than about 5 percent by weight of the total composition.

11. An oral health composition comprising an effective amount of an aldehyde selected from the group consisting of octanaldehyde, nonanaldehyde, undecylenic aldehyde, undecylic aldehyde, dodecyl aldehyde, methylnonylacetaldehyde to inhibit the acid production and growth of oral microorganisms and a dental vehicle.

12. The composition of claim 11 wherein said aldehyde is present in no more than about 5 percent by weight of the total composition.

13. An oral health composition comprising an effective amount of dialdehyde starch to inhibit the acid production and growth of oral microorganisms and a dental vehicle.

14. The composition of claim 13 wherein said dialdehyde starch is present in no more than about 5 percent by weight of the total composition.

15. An oral health composition comprising an effective amount of dialdehyde galactomannan gum to inhibit the acid production and growth of oral microorganisms and a dental vehicle.

16. The composition of claim 15 wherein said dialdehyde galactomannan gum is present in no more than about 5 percent by weight of the total composition.

* * * * *